US012667472B2

(12) United States Patent
Major et al.

(10) Patent No.: US 12,667,472 B2
(45) Date of Patent: Jun. 30, 2026

(54) METHOD AND SYSTEM TO ACTIVATE LIMB MOVEMENT IN AMPUTEES

(71) Applicants: Northwestern University, Evanston, IL (US); U.S. Govt. as rep by the Dept. of Veterans Affairs, Washington, DC (US)

(72) Inventors: Matthew Justin Major, Chicago, IL (US); Riley Marshall Knox, Mill Valley, CA (US); Matthew Lawrence Elwin, Chicago, IL (US); Yael Ben Shalom, Mountain View, CA (US)

(73) Assignees: THE UNITED STATES GOVERNMENT AS REPRESENTED BY THE DEPARTMENT OF VETERANS AFFAIRS, Washington, DC (US); NORTHWESTERN UNIVERSITY, Evanston, IL (US)

( * ) Notice: Subject to any disclaimer, the term of this patent is extended or adjusted under 35 U.S.C. 154(b) by 14 days.

(21) Appl. No.: 17/705,665

(22) Filed: Mar. 28, 2022

(65) Prior Publication Data

US 2022/0346981 A1 Nov. 3, 2022

Related U.S. Application Data

(60) Provisional application No. 63/183,295, filed on May 3, 2021.

(51) Int. Cl.
*A61F 2/70* (2006.01)
*A61F 2/76* (2006.01)
(Continued)

(52) U.S. Cl.
CPC ............... *A61F 2/70* (2013.01); *G16H 20/30* (2018.01); *G16H 40/63* (2018.01);
(Continued)

(58) Field of Classification Search
CPC .................. A61F 2/70; A61F 2002/701; A61F 2002/704; A61F 2002/764; G16H 20/30; G16H 40/63
See application file for complete search history.

(56) References Cited

U.S. PATENT DOCUMENTS

| | | | | | |
|---|---|---|---|---|---|
| 2008/0243265 A1* | 10/2008 | Lanier | ..................... | A61F 2/583 | |
| | | | | | 600/587 |
| 2010/0049333 A1* | 2/2010 | Endo | ........................ | A61H 3/00 | |
| | | | | | 602/5 |

(Continued)

OTHER PUBLICATIONS

Michael D. Lewek et al., Arm Swing magnitude and asymmetry during gait in the early stages of Parkinson's disease. Gait & Posture, Feb. 2010, vol. 31: pp. 256-260.
(Continued)

*Primary Examiner* — Jerrah Edwards
*Assistant Examiner* — Maximilian Tobias Spencer
(74) *Attorney, Agent, or Firm* — Ballard Spahr LLP

(57) ABSTRACT

A limb activation system includes a sensor configured to monitor movement of a user. The system also includes a processor operatively coupled to the sensor and configured to determine, based on the movement of the user, that the user is engaged in walking or running. The processor is also configured to generate an activation signal responsive to the determination that the user is engaged in walking or running. A data-based model integrates sensor information to drive activation and arm swing of the affected upper limb.

19 Claims, 13 Drawing Sheets

(51) Int. Cl.
  *G16H 20/30* (2018.01)
  *G16H 40/63* (2018.01)

(52) U.S. Cl.
  CPC ... *A61F 2002/701* (2013.01); *A61F 2002/704* (2013.01); *A61F 2002/764* (2013.01)

(56) References Cited

U.S. PATENT DOCUMENTS

| | | | | |
|---|---|---|---|---|
| 2011/0257765 A1* | 10/2011 | Evans | A61F 2/581 | |
| | | | 623/24 | |
| 2012/0283844 A1* | 11/2012 | Langlois | G05B 15/02 | |
| | | | 623/24 | |
| 2014/0188257 A1* | 7/2014 | Ura | A63B 24/0003 | |
| | | | 700/91 | |
| 2014/0288681 A1 | 9/2014 | Watanabe | | |
| 2014/0365169 A1* | 12/2014 | Pham | G01C 22/006 | |
| | | | 702/160 | |
| 2015/0351939 A1* | 12/2015 | van der Merwe | A61F 2/586 | |
| | | | 623/24 | |
| 2018/0036145 A1* | 2/2018 | Jury | A61L 27/165 | |
| 2023/0197242 A1* | 6/2023 | Seifert | A61F 2/70 | |
| | | | 705/2 | |

OTHER PUBLICATIONS

Sebastian O.H. Madgwick, An efficient orientation filter for inertial and inertial/magnetic sensor arrays. Apr. 30, 2010, pp. 1-32, available at http://www.X-io.co.uk/res/doc/madgwick internal re port. pdf.

* cited by examiner

Fig. 1

Cohort demographics

| | Walking task, Prosthesis users | ADL tasks, Prosthesis users | ADL tasks, Able-bodied |
|---|---|---|---|
| Sample size | 10 | 7 | 6 |
| Male/Female | 7/3 | 5/2 | 3/3 |
| Age (yrs) | 49 ± 19 | 49 ± 18 | 35 ± 11 |
| TH/TR* | 3/7 | 0/7 | N/A |

*Transhumeral/transradial level limb loss/deficiency

Fig. 4

| Activity Cohort | WSP |
|---|---|
| Walking | 0.063 ± 0.01 |
| Activities of daily living | |
| Prosthesis users | 0.416 ± 0.05 |
| Able-bodied | 0.439 ± 0.09 |

METHOD AND SYSTEM TO ACTIVATE LIMB MOVEMENT IN AMPUTEES

CROSS-REFERENCE TO RELATED APPLICATION

The present application claims the priority benefit of U.S. Provisional Patent App. No. 63/183,295 filed on May 3, 2021, the entire disclosure of which is incorporated by reference herein.

BACKGROUND

Persons with major arm amputations or congenital limb difference between the shoulder and the wrist often do not swing their remaining arm while walking, despite swinging their other limb if it is without amputation. In the case of full arm amputation at the shoulder joint, there is no arm to swing. This asymmetry in arm swing can be noticed by others, and be embarrassing for some individuals with amputation due to reduced aesthetics and stigma associated with amputation. Importantly, research suggests that this asymmetry in arm swing for persons with upper limb amputation can increase the risk of falling, which is prevalent in persons with upper limb loss. For example, it has been shown that upper-limb prosthesis users experience high rates of falling (i.e., ~30% 2 times/year). Approximately 90% of these falls occur during activities of daily living, with 75% of them occurring during walking. Not only is fall prevalence high in this patient group, but so is fall-related injuries.

SUMMARY

An illustrative limb activation system includes a sensor configured to monitor movement of a user. The system also includes a processor operatively coupled to the sensor and configured to determine, based on the movement of the user, that the user is engaged in walking or running, as opposed to manual tasks involving reach and grasp activities. The processor is also configured to generate an activation signal responsive to the determination that the user is engaged in walking or running and guides elbow rotations to match a walking cadence or a running cadence.

The system can also include a sensory stimulator mounted to the user, where the activation signal triggers the sensory stimulator to alert the user to perform movement during the walking or running. In some embodiments, the sensory stimulator can be a vibration stimulator, a pressure stimulator, a skin stretching stimulator, or an auditory stimulator. The system can also include a motor integrated into a prosthetic limb of the user, where the activation signal triggers movement of the motor which results in movement of the prosthetic limb. The system can also include a trajectory generator, and the processor can use the trajectory generator to control cyclical motion of the prosthetic limb. The system can also include a clutch to disengage the motor during an off state.

In an illustrative embodiment, the processor determines a cadence of the walking or running based on the determined movement of the user, and the activation signal is generated based at least in part on the cadence of the walking or running. In another embodiment, the sensor generates a plurality of instantaneous acceleration signals, and the processor is configured to identify repetitive features in the instantaneous acceleration signals and a timing in between the repetitive features to determine the cadence.

The sensor can include an accelerometer, a magnetometer, and/or a gyroscope. In another embodiment, the monitored movement includes frequency data, and the determination that the user is engaged in walking or running is based on the frequency data. In one embodiment, the processor determines a window signal power based on the monitored movement, and the determination that the user is engaged in walking or running is based on the window signal power. In another embodiment, the sensor comprises an accelerometer that generates an acceleration signal, and the processor is configured to process the acceleration signal using a fast Fourier transform (FFT) to determine a single-sided frequency spectrum. In such an embodiment, the processor determines a proportion of the single-sided frequency spectrum that occurs in a time window by generating a first sum of magnitudes of frequency components in the time window and dividing the first sum by a second sum of magnitudes of frequency components across all frequencies. This method can be tuned and optimized for individual users through machine learning techniques.

An illustrative method of activating a limb includes monitoring, by a sensor mounted to an arm, waist, or a prosthetic limb of a user, movement of the user. The method also includes determining, by a processor operatively coupled to the sensor and based on the movement of the user, that the user is engaged in walking or running. The method further includes generating, by the processor, an activation signal responsive to the determination that the user is engaged in walking or running. The method can also include activating, by the processor and responsive to the activation signal, a sensory stimulator mounted to the user, where the sensory stimulator alerts the user to perform movement during the walking or running.

In another embodiment, the method includes activating, by the processor and responsive to the activation signal, a motor incorporated in the prosthetic limb to cause movement of the prosthetic limb. The method can also include determining, by the processor, a cadence of the walking or running based on the movement of the user, where the activation signal is generated based at least in part on the cadence. In another embodiment, the sensor comprises an accelerometer that generates a plurality of instantaneous acceleration signals, and the method includes identifying, by the processor, repetitive features in the instantaneous acceleration signals and a timing in between the repetitive features to determine the cadence. The method can also include determining, by the processor, a window signal power based on the monitored movement, where the determination that the user is engaged in walking or running is based on the window signal power.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 1 is a table that shows study participant demographics in accordance with an illustrative embodiment.

FIG. 4 is a table that depicts results of the study in accordance with an illustrative embodiment.

DETAILED DESCRIPTION

Figures 2A, 2B:
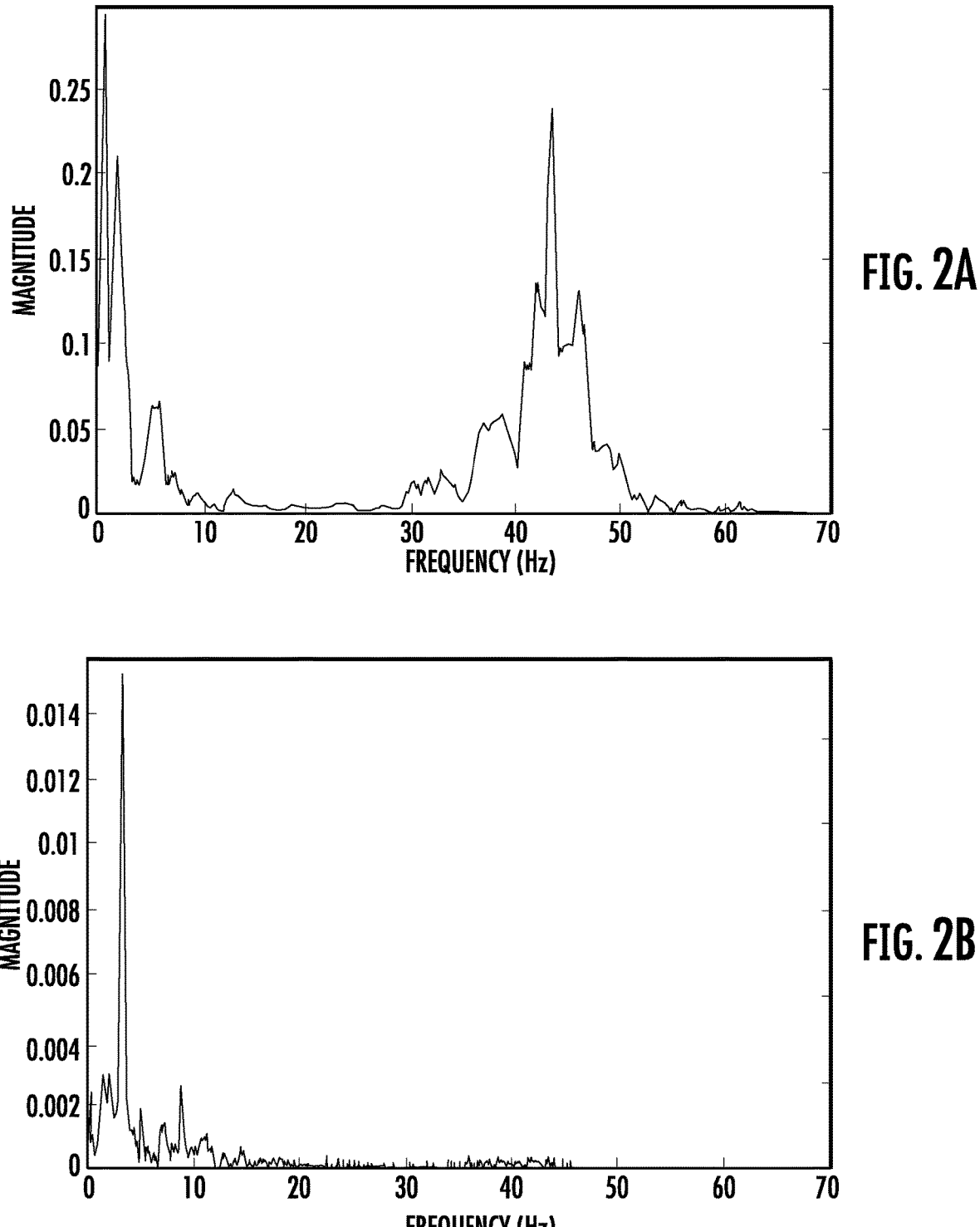
FIG. 2A depicts the acceleration fast Fourier transform (FFT) for test participants during activities of daily living (ADL) in accordance with an illustrative embodiment.
FIG. 2B depicts the acceleration fast Fourier transform (FFT) for test participants during walking in accordance with an illustrative embodiment.

Persons with major arm amputations or congenital limb difference between the shoulder and wrist often do not swing their remaining arm while walking, despite swinging their other limb if it is without amputation. Currently available arm prostheses do not actively swing the prosthesis during walking, and there is no technology to encourage arm swing in persons with upper limb loss. Described herein is wearable technology that will automatically identify if a person is walking or running and remind them to swing their remaining limb through providing a subtle touch or noise cue, or activate a motorized prosthetic elbow or shoulder to swing in cycles that match their leg swing. The device can be worn under clothing and integrated into their arm prosthesis for discreteness. Restoring arm swing in persons with arm amputation or congenital limb difference can improve the aesthetics of walking and symmetry of movement. Improving symmetry of movement can also help balance the body for improved steadiness during walking and running, which reduces the likelihood of a fall and associated injury.

The proposed methods and systems can restore arm swing to improve walking aesthetic, avoid stigma of upper limb loss, and improve balance during walking and running, benefits which will improve quality of life for amputees. This technology can be wearable and can include hardware and software to collect instantaneous acceleration (e.g., from an accelerometer), magnetic field direction (e.g., from a magnetometer), and angular velocity (e.g., from a gyroscope) information to process, analyze, and classify movement activity in real-time. As movement activity is classified, the system determines if the wearer is walking or running. More specifically, the system software reads instantaneous movement data of wearer through accelerometer and/or gyroscope sensors, and uses the frequency content of that data to classify activities as either walking/running or any other tasks including manual tasks with the arms. This software then communicates with external hardware to produce a stimulus and/or activate a prosthetic elbow or shoulder to induce wearer arm swing in the amputated/prosthetic limb.

In an illustrative embodiment, once walking or running activity is verified, the system activates arm swing through one of two modes. For wearers with amputation below the elbow, the wearer can receive epidermal (e.g., vibration, pressure, or skin stretching) or auditory stimulus to remind the wearer to swing their arm while walking or running in synchrony with a cadence. For wearers with amputation above the elbow, the system activates a motorized prosthetic elbow or a motorized prosthetic shoulder that begins swinging while walking or running in synchrony with a cadence that also serves to remind the wearer to swing their arm at the shoulder if the user had a transhumeral level amputation. The system is non-invasive and discrete. In the case of wearers with amputation below the elbow, the system can be worn under the clothes and attached to the remaining arm. In the case of wearers with amputation above the elbow, the system is installed within a modular prosthetic elbow or prosthetic shoulder that can be integrated into any arm prosthesis.

To properly develop methods that aim to reduce the risk of falling while walking, the act of walking itself had to be distinguished from other activities involving the arms. A study was therefore conducted to analyze kinematic data obtained during walking and other activities of daily living (ADLs) to identify methods by which the activity being performed may be classified. The study was divided into two parts: i) walking trials, and ii) reach and grasp trials simulating upper-limb ADLs. Subject groups for each part did not overlap.

Ten individuals (7 male, 3 female; average age 49±19 years) with unilateral upper-limb amputation (ULA) (7 transradial, 3 transhumeral) participated in the walking trials and were outfitted with reflective markers on their trunk, pelvis, legs, and arms, including prosthesis. FIG. 1 is a table that shows study participant demographics in accordance with an illustrative embodiment. Participants walked at a self-selected pace while marker position data were collected at a frequency of 120 Hertz (Hz) using a 12-camera motion capture system (Motion Analysis Corp., CA).

For the reach and grasp trials, seven individuals with unilateral transradial ULA (5 male, 2 female; age 49±18 years) and six able-bodied persons (3 male, 3 female; age 35±11 years) were outfitted with reflective markers on their trunk, pelvis, and arms (intact and prosthesis, if applicable). Participants performed a series of ADLs including cutting food, turning a page, unimanual lifting and pouring a carton, unimanual lifting and transferring a weighted container, and bimanual lifting and transferring a tray. Participants with ULA performed tasks using the prosthetic side, while able-bodied participants used the non-dominant hand. Marker position data were collected at 120 Hz using the 12-camera motion capture system.

Marker coordinate data for both studies were analyzed using MATLAB (MathWorks, MA). Acceleration at the elbow was calculated as the second derivative of elbow marker position using equation 1 below, and the Pythagorean Theorem was used to calculate overall magnitude of the acceleration using equation 2:

$$\alpha_i = \frac{i_3 + i_1 - 2i_2}{(\Delta t)^2} \qquad \text{Equation 1}$$

$$\alpha_3 = \sqrt{\alpha_x^2 + \alpha_y^2 + \alpha_z^2} \qquad \text{Equation 2}$$

Acceleration was calculated for the prosthetic side elbow in walking trials. Acceleration was also calculated at the prosthetic side and non-dominant side for the prosthesis user group and able-bodied group in reach and grasp trials, respectively. The fast Fourier transform (FFT) of the acceleration signal was calculated. The strength of the FFT signal in the window 37-48 Hz (i.e., window signal power (WSP)) was calculated by summing the signal power at all frequencies in the range and dividing by the sum of signal power across all frequencies. Average WSP was calculated for the following groups: walking trials, ULA reach and grasp, and able-bodied reach and grasp. Groups were compared statistically using the independent t-test or Mann-Whitney U test based on data normality as assessed with the Shapiro-Wilk test ($\alpha$=0.05). FIG. 2A depicts the acceleration fast Fourier transform (FFT) for test participants during activities of daily living (ADL) in accordance with an illustrative embodiment. FIG. 2B depicts the acceleration fast Fourier transform (FFT) for test participants during walking in accordance with an illustrative embodiment.

Figure 3:
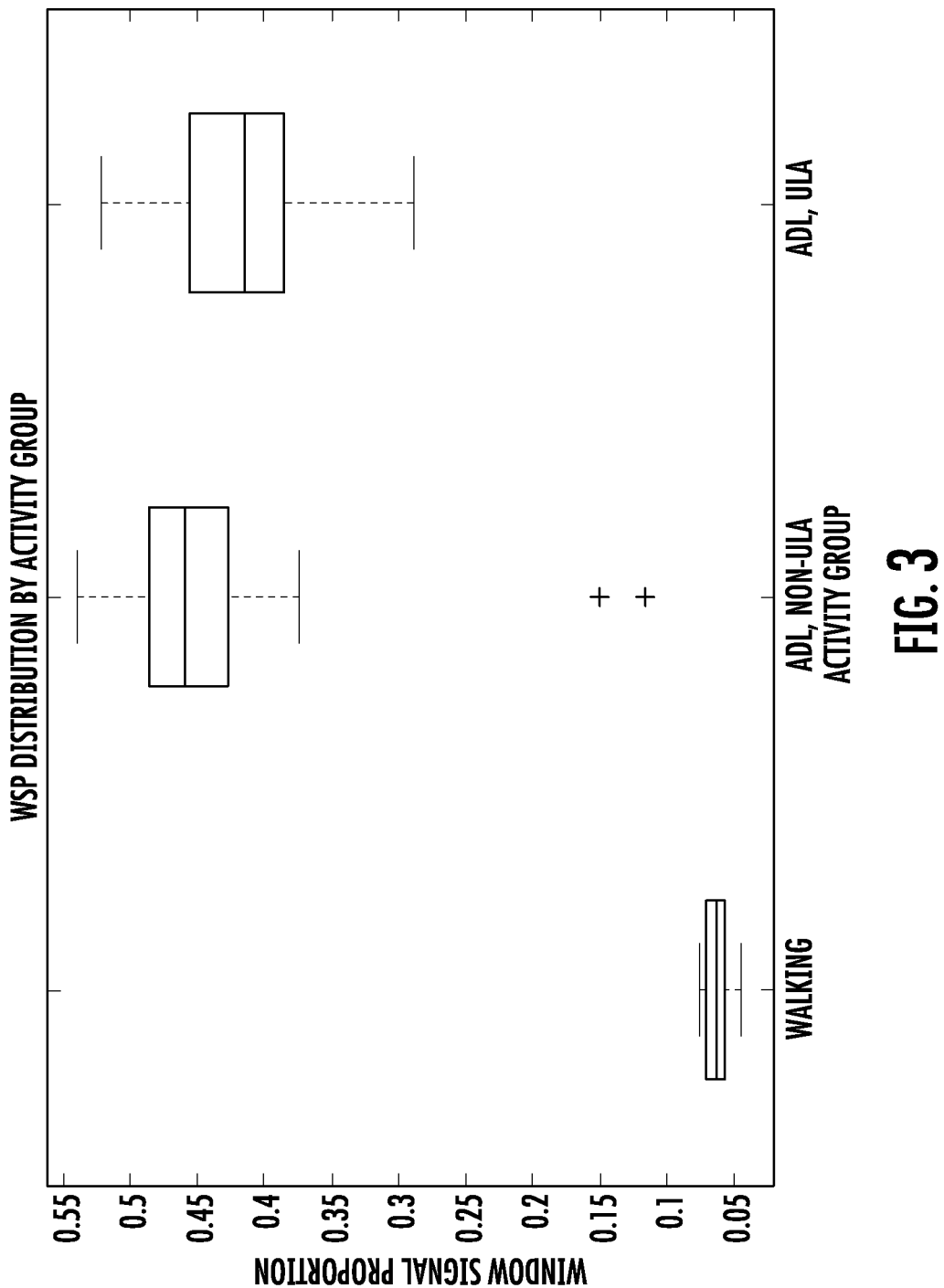
FIG. 3 depicts window signal proportion (WSP) distribution by activity group in accordance with an illustrative embodiment.

FIG. 3 depicts window signal power (WSP) distribution by activity group in accordance with an illustrative embodiment. Walking trials had an average WSP of 0.063±0.010. For reach and grasp trials, the ULA group had an average WSP of 0.416±0.054 and the able-bodied group had an average WSP of 0.439±0.091. Average WSP was significantly lower for walking when compared to both the ULA (p<0.001) and non-ULA (p<0.001) groups in reach and grasp trials, with no significant difference (p=0.233) between the ULA and non-ULA groups in reach and grasp trials. Results suggest that the FFT of elbow acceleration has different properties when walking versus performing reach and grasp tasks with the arms.

FIG. 4 is a table that summarizes the above-discussed results of the study in accordance with an illustrative embodiment. The results of the study suggest that the frequency spectrum of 3-dimensional elbow acceleration has different properties when walking versus using the arms for upper limb ADLs. These differences can be used as an effective measure to distinguish between walking and upper limb ADLs when recording or analyzing real-time movement behavior on the prosthesis. Also, similarities between prosthesis users and able-bodied cohorts performing the same ADLs suggest that a task classification algorithm can be trained using data from both groups. This is further illustrated by the similarity in relevant signal power between the ULA and able-bodied groups in reach and grasp tasks. Together, this data indicates that acceleration frequency analysis can be a useful subject-independent tool in developing activity classification algorithms for use in assistive devices. The study also indicates that acceleration signal FFT analysis is a useful and simple method for upper-limb task classification. Additionally, it was shown that elbow motion frequency analysis can be an effective measure to distinguish between engagement in upper-limb goal-oriented tasks and walking in persons with ULA to record real-time movement behavior.

Figure 5:
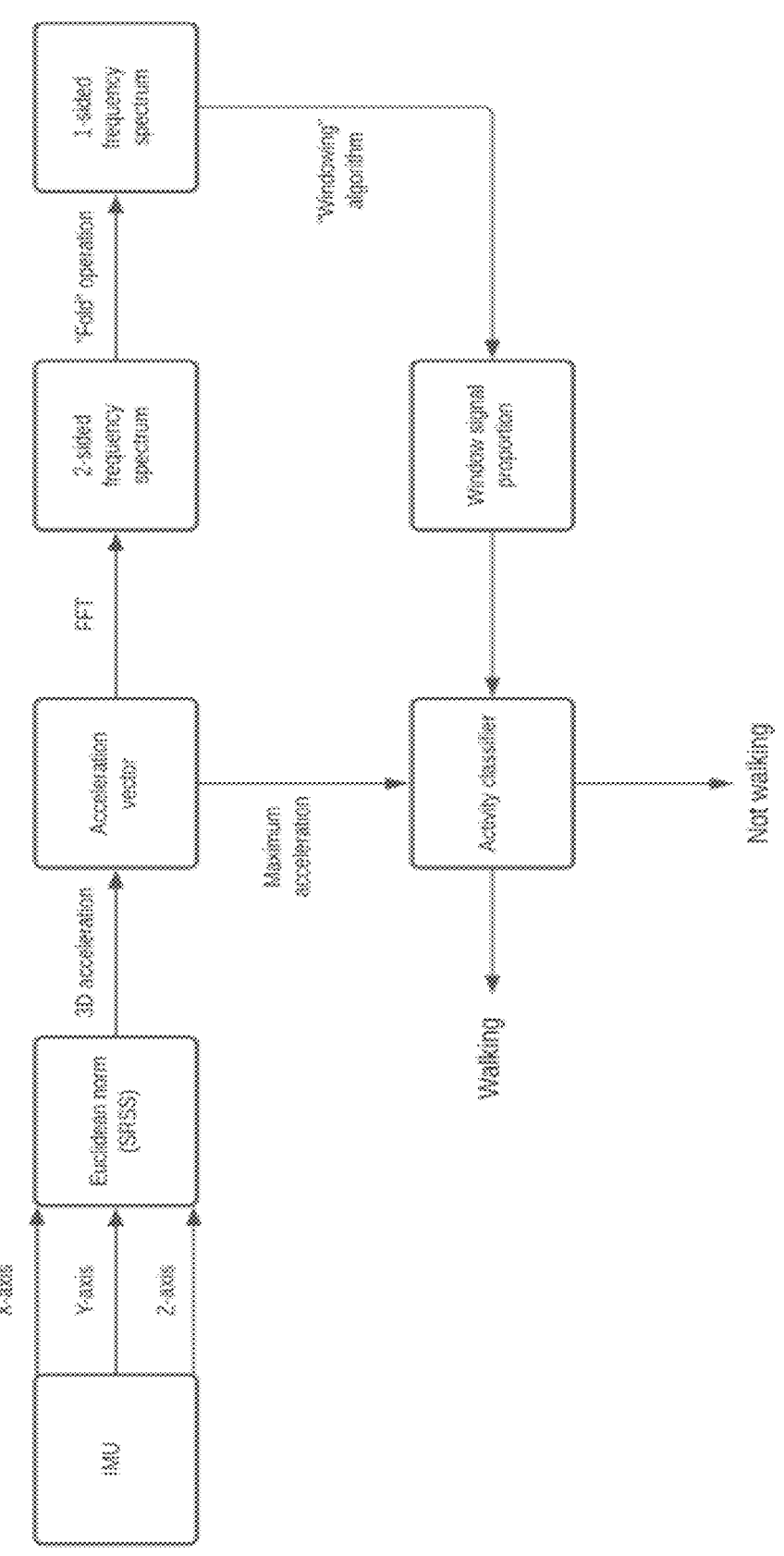
FIG. 5 is a flow diagram that depicts an activity classification algorithm in accordance with an illustrative embodiment.

FIG. 5 is a flow diagram that depicts an activity classification algorithm in accordance with an illustrative embodiment. In alternative embodiments, fewer, additional, and/or different operations may be performed. Also, the use of a flow diagram is not meant to be limiting with respect to the order of operations performed. As shown, instantaneous three-dimensional acceleration data is acquired at 150 Hz by an embedded inertial measurement unit (IMU) that can include an accelerometer sensor, a magnetometer sensor, and/or a gyroscope sensor. An obtained acceleration signal is processed using a Fast Fourier Transform to return the single-sided frequency spectrum. The proportion of the frequency spectrum occurring in a certain window is determined by summing the magnitudes of frequency components in that window and dividing by the sum of magnitudes across all frequencies. Activity classification is performed using the window signal proportion and maximum value in the acceleration signal. Walking or running (as opposed to manual activities) is identified if maximum acceleration is below a first predetermined threshold (e.g., 0.1) and window signal proportion is above a second predetermined threshold (e.g., 0); see FIG. 3 and FIG. 4. To properly time the arm swing control signal, step cadence is determined by identifying and timing repetitive features in the instantaneous acceleration signal and thereby coordinating the signal. In an illustrative embodiment, gyroscope data and/or magnetometer data can be integrated into the classification algorithm for additional validation of the occurrence of a walking or running activity.

Figure 6:
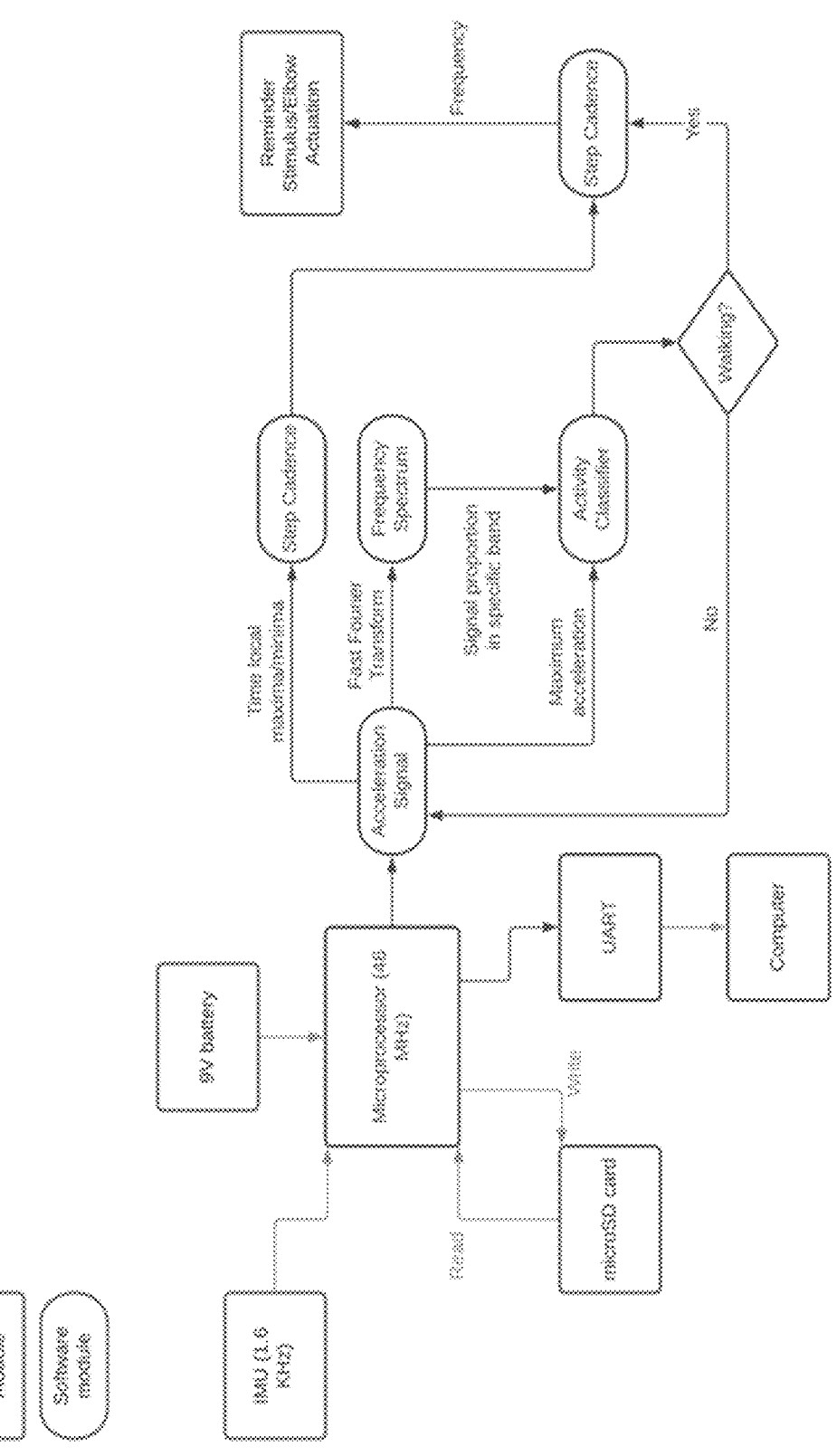
FIG. 6 depicts software and hardware of a wearable system in accordance with an illustrative embodiment.

FIG. 6 depicts software and hardware of a wearable system in accordance with an illustrative embodiment. In one embodiment, the device can be powered by a 9-volt battery whose output is reduced by a linear drop-off regulator to the level required by the embedded microprocessor. Alternatively a lithium ion battery or other power source may be used. The processor can be a 32-bit microcontroller operating at its maximum speed of 48 MHz, programmed with the data acquisition and processing algorithm described herein. Alternatively, a different processor may be used. In one embodiment, the processor receives data at 150 Hz from an onboard 3-axis inertial measurement unit (IMU) containing both an accelerometer and a gyroscope in a single package. The IMU measurements are performed at 1.6 KiloHertz (KHz) with a one-measurement data buffer, meaning approximately one of every ten measurements is sent to the processor. Communication between the processor and IMU is done over serial peripheral interface (SPI) at 12 megaHertz (MHz). The system can be outfitted with connections to store data on an onboard microSD card or other memory, and these data may be used for algorithm refinement. Communication between the processor and microSD module is done over a Serial Peripheral Interface (SPI). The wearable device may also be connected to a computer to stream data over a serial port using a universal asynchronous receiver/transmitter (UART) module. Once walking is detected per the algorithm described above, the processor sends a signal to an attached hardware module to remind the wearer to swing their arm. In the case of a tactile stimulus such as a vibration motor, the signal activates the stimulus during walking or running, with the activation signal being sent at a frequency that matches step cadence. Alternatively, once walking is detected, a motor is activated to assist with arm movement. A motorized version of the system is described in more detail below.

In an illustrative embodiment, the device software classifies the wearer's behavior into walking/running versus upper-limb activities by performing a Fast Fourier Transform on an acquired three-dimensional acceleration signal, then analyzing the resultant frequency spectrum for identifying factors. The internal device software (task classification algorithm, etc.) were written in C, with external computer modules written in Python. Software is installed on a Microchip PIC32 processor and interfaces with an external inertial measurement unit. No operating system is required beyond the native microprocessor. Software distribution can be done as object code installed on the native processor. In alternative embodiments, different components and/or a different configuration may be used.

Figure 7:
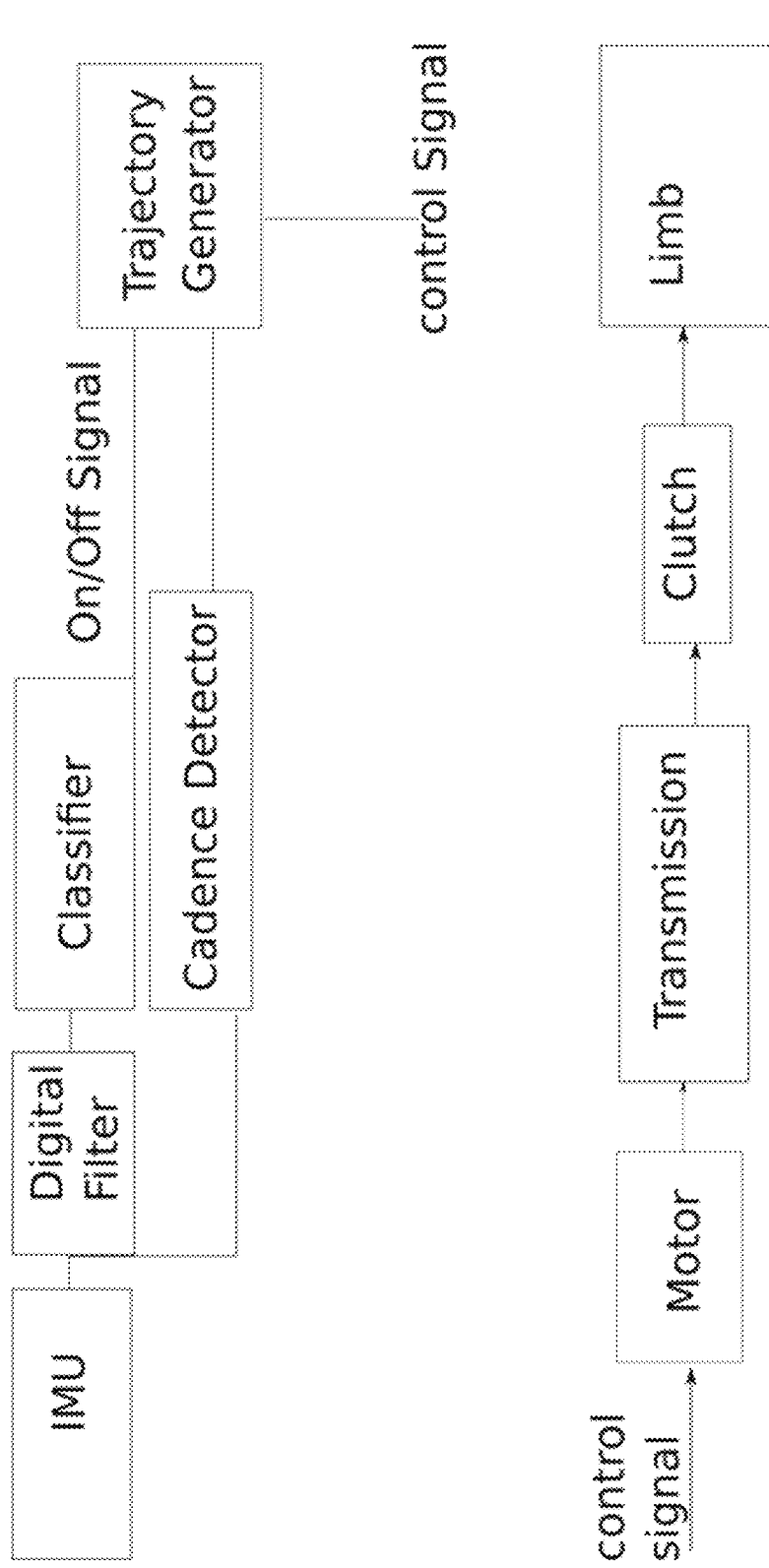
FIG. 7 is a logic diagram depicting system operations and interactions in accordance with an illustrative embodiment.
Figure 8:
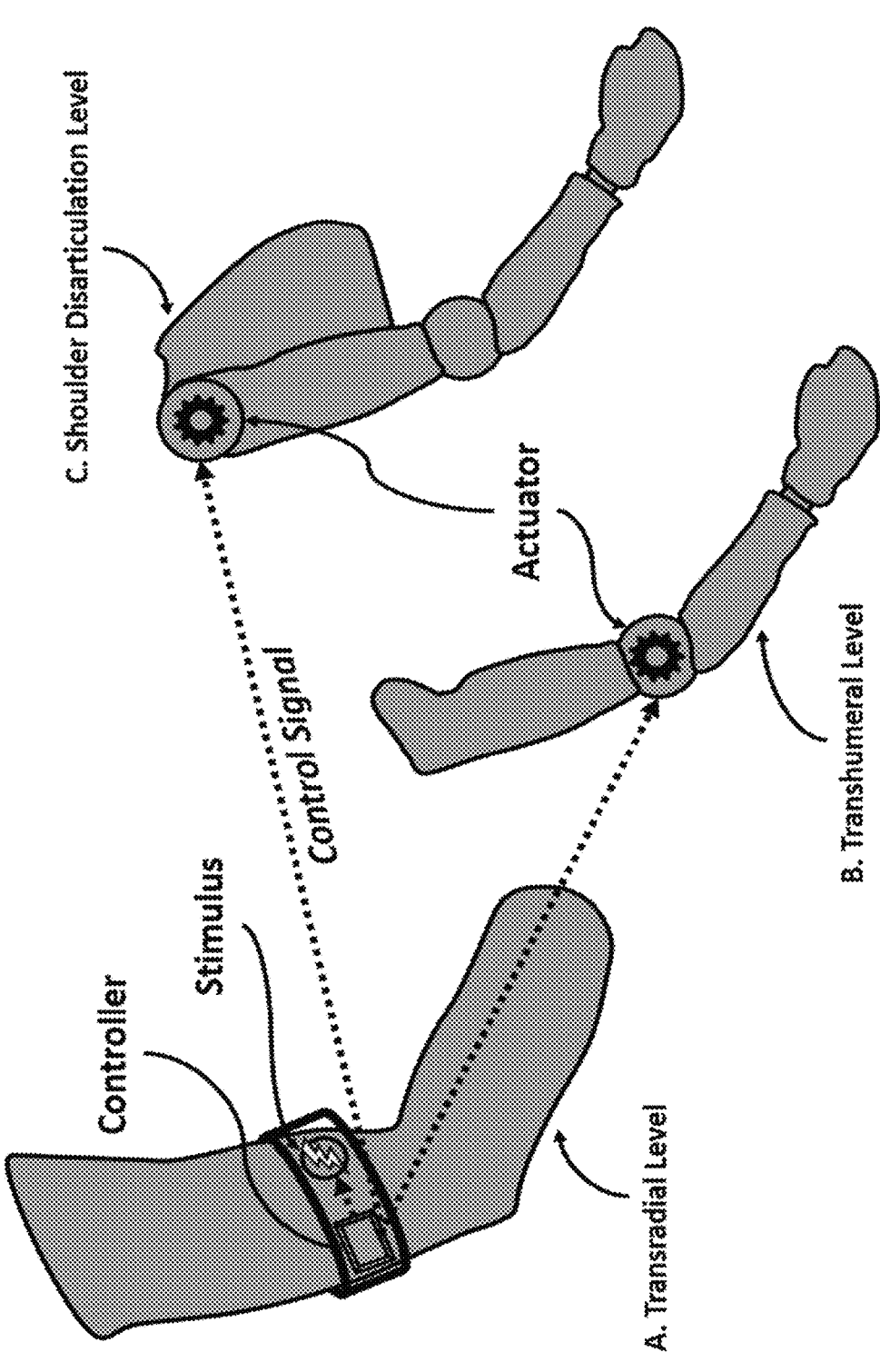
FIG. 8 depicts wearable configurations for different users in accordance with an illustrative embodiment.

FIG. 7 is a logic diagram depicting system operations and interactions in accordance with an illustrative embodiment. FIG. 8 depicts wearable configurations for different users in accordance with an illustrative embodiment. In operation, for transradial (below-elbow) amputees, once the wearable system detects walking at any speed or running, as opposed to other activities (e.g., manual tasks with the arms), the system delivers a repeated (on/off pulse cycle) vibration sensation on the skin through a vibrating motor (or vibrator), a pressure sensation on the skin through a solenoid, voice coil, piezoelectric, or other linear actuator, a stretch sensation on the skin through a piezo-electric, electrostatic or electro-magnetic actuator, and/or an audible noise through a small speaker to remind the wearer to swing their arm at the shoulder and/or elbow joint (depending on the user). The frequency of the stimulus is synchronized to the determined cadence of the activity. In an illustrative embodiment, the sensation delivery function can be toggled off if the wearer does not want to use this function.

In one embodiment for transhumeral or shoulder (above-elbow) amputees, once the wearable system detects walking at any speed or running, as opposed to other activities (e.g., manual tasks with the arms), the system activates cyclical flexion and extension (single plane of action) of a robotic (motor actuated) elbow or shoulder joint. For transhumeral level amputation, the elbow action also serves to remind the wearer to swing their arm at the shoulder joint. The frequency of the elbow or shoulder swing can be synchronized to the determined cadence. The elbow or shoulder swing actuation feature can either be integrated with an existing motor actuated prosthetic elbow or shoulder to drive cyclical flexion/extension, or a modular prosthetic elbow or shoulder component that has free motion when not walking/running such that it can be body powered for manual tasks. The automatic elbow or shoulder swinging function can be toggled off if the wearer does not want to use this function.

As discussed in more detail below, the actuation of the arm can be produced by a motor. The motor can be located either at the shoulder joint or the elbow joint. The output shaft of the motor may be directly connected to the arm or it may be connected to a transmission, a transmission and a clutch, or to a clutch. The transmission converts the range of torques and speeds produced by the motor into a range of torques and speeds necessary for arm actuation. The purpose of the clutch, when used, is to decouple the motor and transmission from the arm movement when the user toggles the functionality off. The clutch can be engaged/disengaged either mechanically by the user, electronically by the user with a button, or automatically by the software. The clutch may also be implemented in software on the computer. For example, the computer can take sensor signals from some combination of the accelerometer, gyroscope, and encoders placed in the elbow joint, on the motor, and in the transmission, and compute a control signal that causes the motor to move in concert with the user adjusting the prosthetic. If the drive system is backdrivable, the clutch may be omitted.

The transmission may also contain a flexible element such as a torsional spring or flexure. This flexure connects the input (from the motor or other gearing) to the output (the arm limb). An encoder is placed on either side of the flexure to measure its displacement. Knowing the stiffness of the flexure, the torque applied to the arm can be measured. By sensing this torque, the arm control signal can be adjusted to accommodate the user adjusting the arm with their opposite limb.

The motor can be placed in either the upper or lower limb segment (or both) depending on the size characteristics of the prosthesis, including the radius and length of the lower and upper arms. If the motor is in the upper arm, it remains fixed as the lower arm swings. If the motor is in the lower arm, it moves along with the swinging. The cyclical motion of the actuation can be controlled by a trajectory generator. The trajectory generator takes two input signals: an on/off signal from the motion classifier and output from a cadence detector. The on/off signal activates the trajectory generator only when walking or running is detected. The cadence detector measures and filters the frequency content in the motion to send an arm swing signal based on the dominant walking frequency. This signal is used to adapt a baseline open-loop cyclical trajectory created internally by the trajectory generator to an individual's walking/running tempo.

To better predict arm-body motion, the inventor also analyzed arm movement data patterns, simulated full arm dynamics, and found the relation between walking speed to angular velocity of the arm. For this analysis, data collection was focused primarily on measuring prosthesis characteristics and collecting body-arm motion data.

Figure 9A:
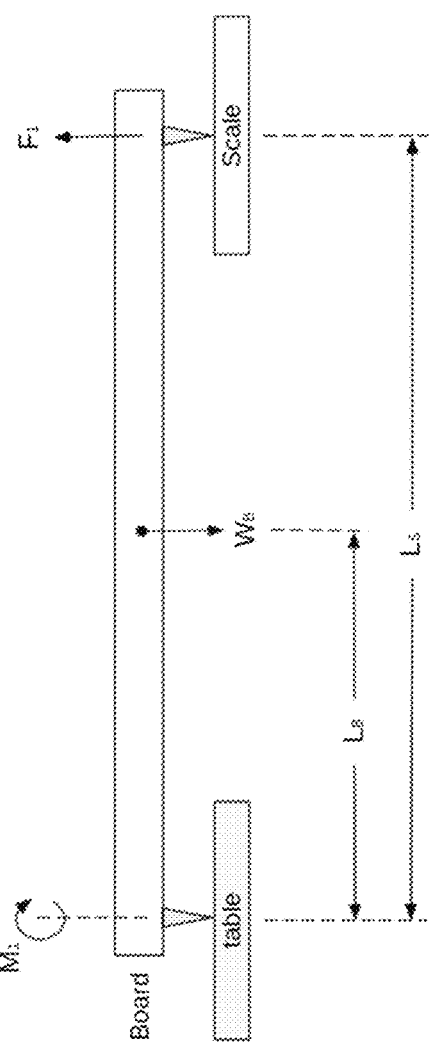
FIG. 9A depicts the COM estimation system in accordance with an illustrative embodiment.

To get the size and mass of an average prosthesis to model and develop the motor control system, more than 20 different prosthetic arms were measured. To find the center of mass (COM) location, a center-of-mass estimation system was used. The COM estimation system included a wooden board with nails on both sides and a digital scale (i.e., reaction or moment board technique). One side of the board was located on the scale, and the other side was located on a leveled table. FIG. 9A depicts the COM estimation system in accordance with an illustrative embodiment.

In a first operation, the center of mass of the wooden board was determined. The COM of the board was derived using the Torque Equilibrium equation for the system, as follows:

$$\sum M_1 = F_1 \cdot L_s - W_B \cdot L_B = 0 \qquad \text{Equation 3}$$

$$L_B = \frac{F_1 \cdot L_S}{W_B}, \qquad \text{Equation 4}$$

where $W_B = m_B g$ is the weight of the board.

Figure 9B:
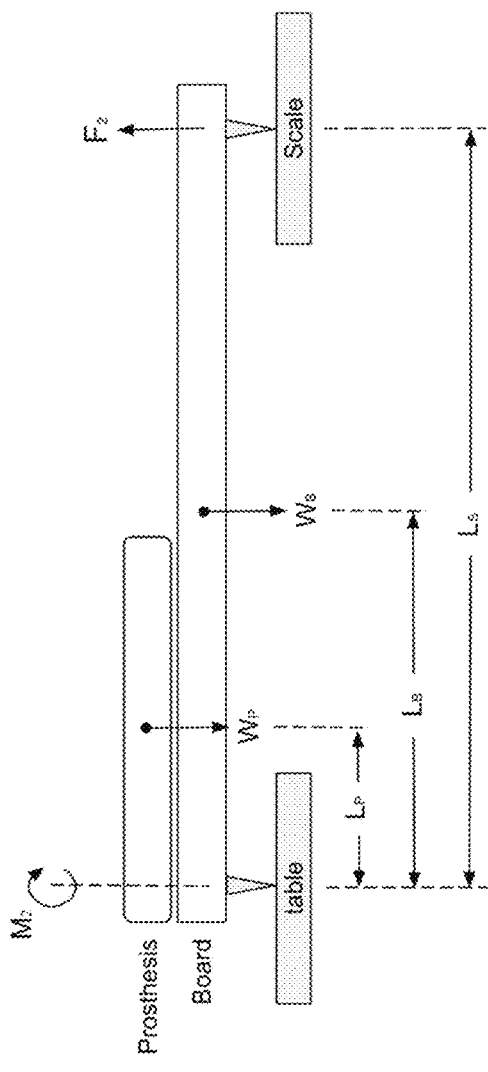
FIG. 9B depicts the COM estimation system in use to determine the center of mass of a prosthesis in accordance with an illustrative embodiment.

Similarly, the COM of a prosthesis can be found by locating it above the wooden board and examining the change in the Torque Equilibrium equation, as depicted in FIG. 9B. Specifically, FIG. 9B depicts the COM estimation system in use to determine the center of mass of a prosthesis in accordance with an illustrative embodiment. The COM of the prosthesis was calculated using the above-discussed Torque Equilibrium equation on the system in FIG. 9B, as follows:

$$\sum M_2 = F_2 \cdot L_s + W_P \cdot L_P - W_B \cdot L_B = 0 \qquad \text{Equation 5}$$

$$L_P = \frac{F_2 \cdot L_S - W_B \cdot L_B}{W_P}. \qquad \text{Equation 6}$$

Body-arm motion measurements were also conducted. Specifically, to explore the body-arm motion while walking, and to find the correlation between walking speed and arm swing, motion capture was used to measure arm dynamics of 13 able-bodied (non-amputee) persons, and inertial measurement units (accelerometers, a magnetometer, and a gyroscope) were attached to a single able-bodied subject's lower back, upper arm, and forearm. Position, angles, velocities, and accelerations were measured, and the shoulder angels and elbow angles were computed. This measured data was used to model arm motion, and to establish a kinematic relationship between walking speeds and elbow joint range-of-motion. To better understand the motion of a human arm and find a suitable motor to imitate the elbow motion, the arm was modeled as a double pendulum system. The system Lagrangian was used and shoulder and elbow angles were determined to find the motion equations and extract the required elbow torque.

Figure 10:
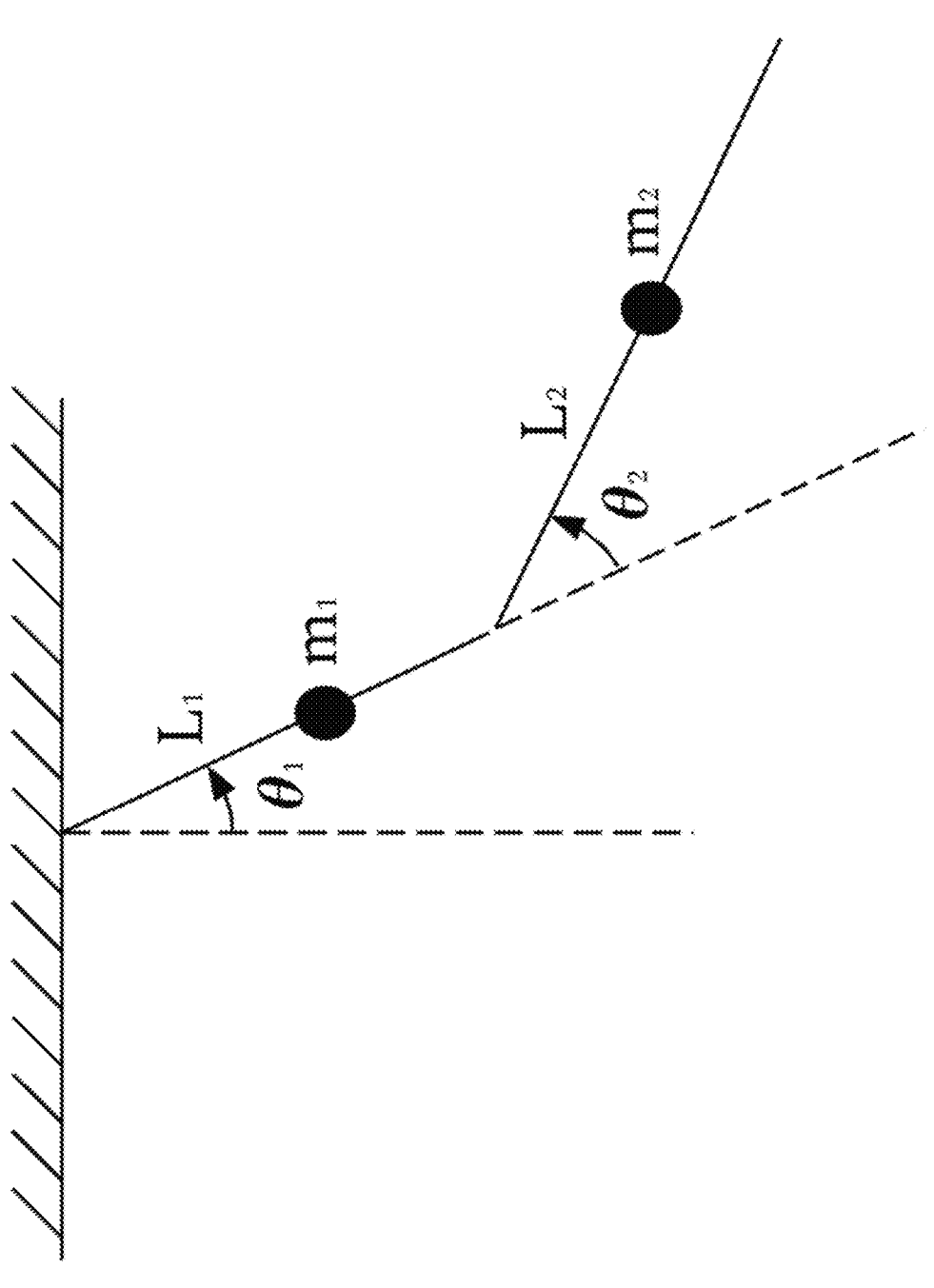
FIG. 10 depicts a representation of the double pendulum system used, in which masses are located at the center of mass of each link in accordance with an illustrative embodiment.

FIG. 10 depicts a representation of the double pendulum system used, in which masses are located at the center of mass of each link in accordance with an illustrative embodiment. Referring to FIG. 10, the kinetic and potential energy of the system can be determined as follows:

$$KE = \frac{1}{2} \cdot m_1 \cdot (x_1^2 + y_1^2) + 1/2 \cdot m_2 \cdot (x_2^2 + y_2^2)$$ Equation 7

$$PE = m_1 \cdot g \cdot y_1 + m_2 \cdot g \cdot y_2,$$ Equation 8 where $m_1$ and $m_2$ are masses of the upper arm and the forearm (respectively), R1 and R2 are the distance from the joint to the center of mass of the upper arm and the forearm (respectively), g is the gravity constant, and:

$$x_1 = R_1 \cdot \sin(\theta_1)$$ Equation 9

$$y_1 = -R_1 \cdot \cos(\theta_1)$$ Equation 10

$$x_2 = R_1 \cdot \sin(\theta_1) + R_2 \cdot \sin(\theta_1 + \theta_2)$$ Equation 11

$$y_2 = -R_1 \cdot \cos(\theta_1) - R_2 \cdot \cos(\theta_1 + \theta_2).$$ Equation 12:

The Lagrangian L(t) is the different between the two energies:

$$L(t) = KE - PE$$ Equation 13:

The Euler-Lagrange equation, the connection between the joints torque to the joint angles, can be determined using the following equation:

$$\tau_i(t) = \left(\frac{\partial L}{\partial \dot\theta_i}\right)' - \frac{\partial L}{\partial \theta_i},$$ Equation 14 where i is the joint number. Inserting the measured angles into the equations returns the torque as a function of time. After scanning the maximum torque and velocity over all trials, the maximum requirements for the motor were determined.

Figure 11:
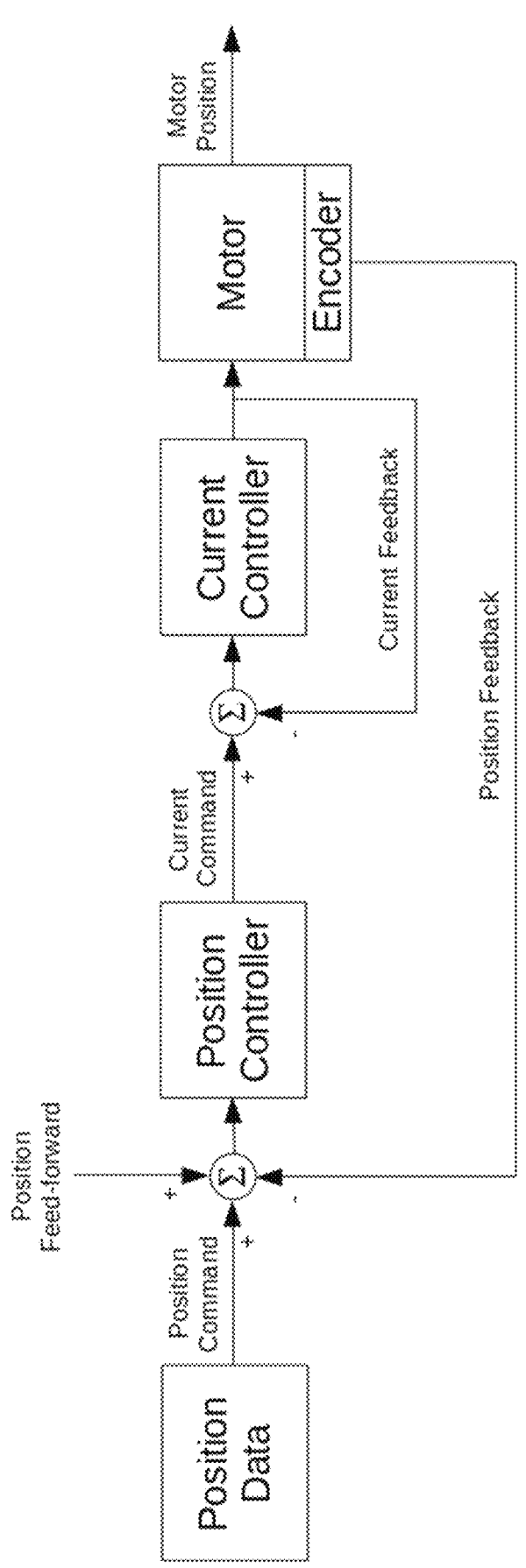
FIG. 11 depicts a motor control system in accordance with an illustrative embodiment.
Figure 12:
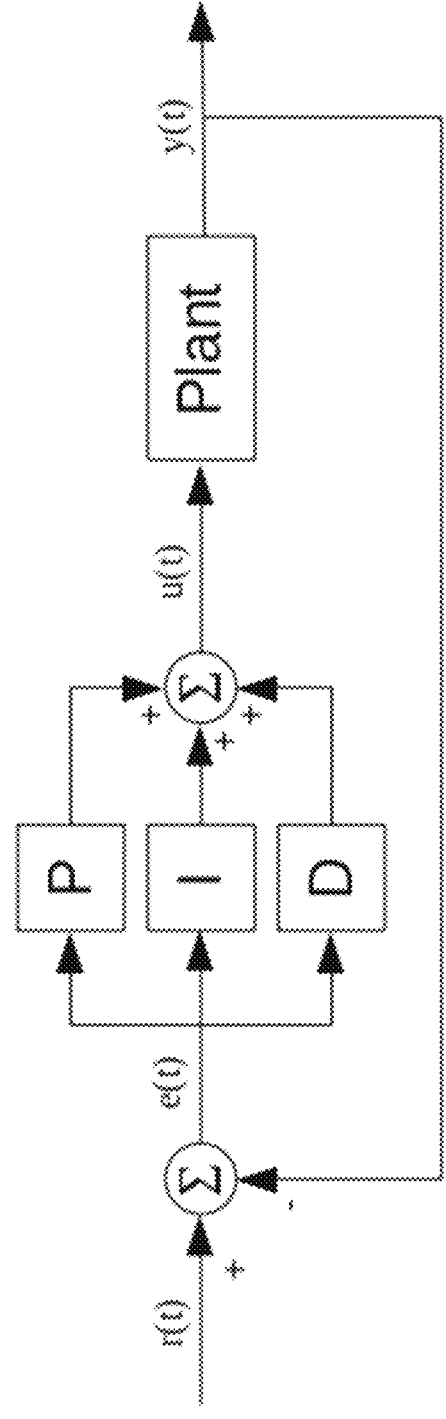
FIG. 12 depicts a proportional-integral-derivative (PID) position control diagram that functions as a second layer of the control system in accordance with an illustrative embodiment.

To define the static torque and weight requirements for the motorized prosthetic elbow, several different transhumeral prostheses representing a range of body-powered device types were characterized. A desired device weight was determined by determining a difference between the masses of the human arm and a proportional prosthetic arm, as follows:

$$M_{Device} = M_{Human\ arm} - M_{Prosthetic\ arm}$$ Equation 15:

The desired device static torque was calculated using the following torque equation, in which W=M·g:

$$T_{Device} = L_{Prosthesis\ COM} \cdot W_{Prosthesis}$$ Equation 16:

Once motor specifications were determined, a control system for the motor was developed. FIG. 11 depicts a first layer of a motor control system in accordance with an illustrative embodiment. FIG. 12 depicts a proportional-integral-derivative (PID) position control diagram that functions as a second layer of the control system in accordance with an illustrative embodiment. As shown, the two layers of the control system include feedback current control and position control. In alternative embodiments, fewer or additional layers may be used. The current of the motor was controlled by an Odrive controller, and the elbow joint angular position was controlled by the feedback PID controller of FIG. 12 (with an optional feedforward component). The PID controller can rely on an established angle-to-speed correlation. In alternative implementations, different types of controllers may be used. As shown in FIG. 11, the control system generates a position command based on position data, which is combined with a model-driven feedback from an encoder of the motor. This combined data is fed to a position controller, which generates a current command that is combined with current feedback and sent to a current controller. The current controller controls the motor such that a desired motor position is achieved.

Over the course of several tests using the above-described control system to control motor position, input angles and output angles were monitored to determine the responsiveness of the motor. After tuning the controller, the error percentage (from the maximum angle) was found to be less than 5%.

Figure 13:
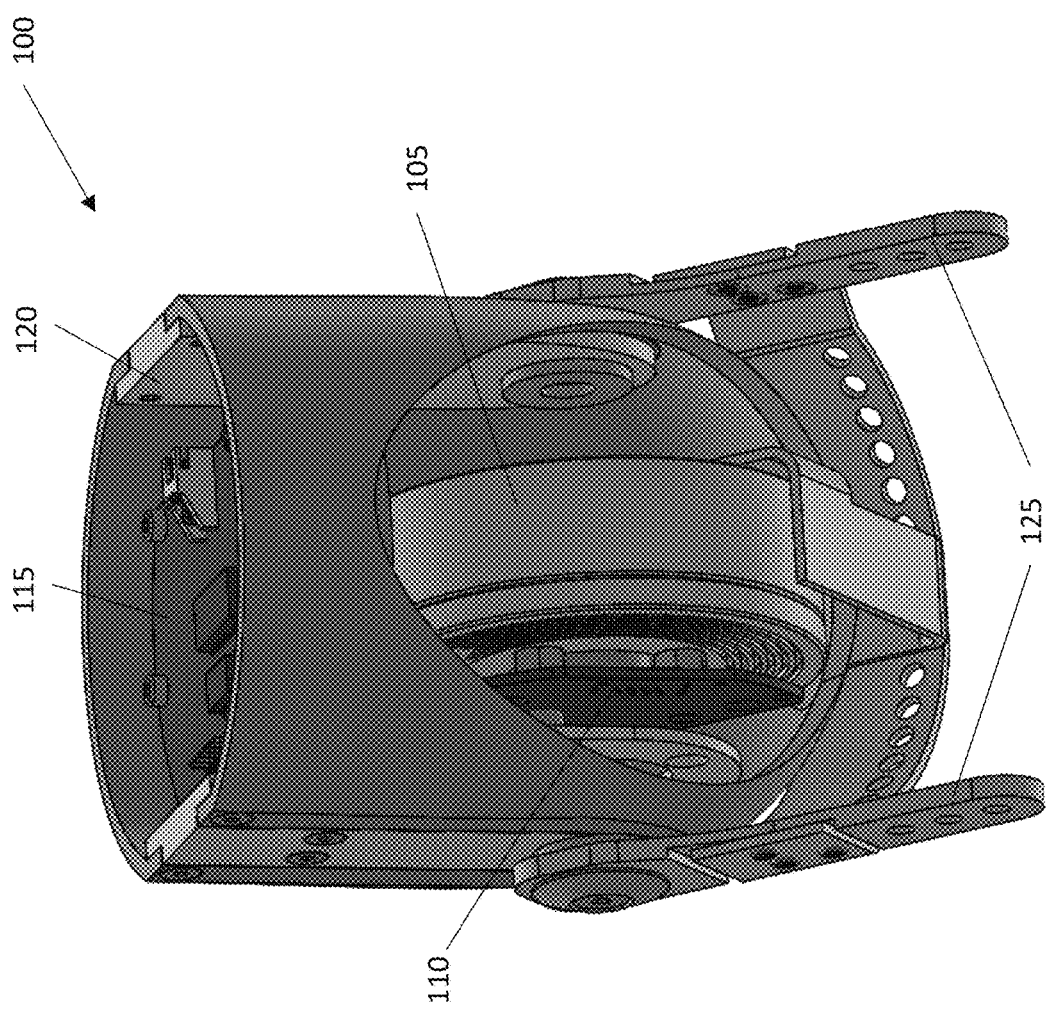
FIG. 13 depicts a motorized limb control system in accordance with an illustrative embodiment.

FIG. 13 depicts a motorized limb control system 100 in accordance with an illustrative embodiment. The motorized limb control system 100 includes a motor 105, a motor encoder printed circuit board (PCB) 110, a main PCB 115, elbow packaging 120, and a lower arm connection 125. In alternative embodiments, the motorized limb control system 100 can include fewer, additional, and/or different components. The system connects to a user's elbow via the elbow packaging 120, and the lower arm connection 125 connects to a lower arm, which can be in the form of a prosthetic. As shown, the lower arm connection 125 includes a pair of bars that mount directly to the prosthetic. The motor 105 is used to move the prosthetic as described herein.

The motor 105 can be any type of electric motor (e.g., T-motor, R60 KV115), and is powered by a power source such as a battery (e.g., alkaline battery, lithium-ion battery, etc.) that also powers the printed circuit board components. The motor encoder PCB 110 is mounted to the motor 105 and includes components that provide closed loop feedback signals based on the tracked speed and/or position of the motor. In one embodiment, the motor encoder can be a magnetic rotary encoder (e.g., AS5048A). Alternatively, a different type of motor encoder may be used. The motor 105 can also include a transmission and/or a clutch as described herein. Alternatively, the clutch may be implemented as software stored in a memory of the main PCB 115.

The main PCB 115 can include a driver (e.g., Odrive V3.6, 24V) and an Odrive adaptor that is used to connect an Odrive connector to an ethernet connector for communication. The main PCB 115 can also include a processor, a memory, and a transceiver (i.e., a transmitter and a receiver) to execute the control and operational algorithms described herein. A user interface (e.g., button, touchscreen, etc.) may also be included to allow the user to control and interact with the system. In an illustrative embodiment, any of the operations/functions described herein can be implemented as computer-readable instructions that are stored in the memory. Upon execution of these instructions by the processor, the system operates as described herein. As an example, the stored instructions can be used for determining that a user is walking or running, implementing motor control algorithms, implementing a trajectory generator, determining a cadence, turning the motor control on/off (automatically or based on user input), communicating with an external computer or database, providing an acoustic or sensory signal to alert the user when he/she should move his/her arm, etc. Advanced machine learning algorithms can also be included to learn the wearer's walking, running, and body movement to update the controller for tuning to each user and optimizing activity detection, control signals, and function to match arm swing and/or sensory feedback to walking/running cadence. Depending on the embodiment, the main PCB 115 can also include or be connected to a speaker to provide an audible movement cue to the user, a vibrator, skin stretching device, pressure device, or other component to provide a tactile movement cue to the user, a motor driver, a current sensor, a gyroscope, an accelerometer, etc.

The methods and systems described herein can be used for restoring arm swing in persons who do not swing their arms normally but have the ability to do so, including pathologies of Parkinson's disease, stroke, arm amputation, Huntington's disease, etc. The system can also be used for physical therapy interventions to train people how to swing their arms. In some implementations, the system can be incorporated into existing arm prostheses to remind a person with amputation to swing the arm through flexion/extension of the remaining elbow and/or shoulder joint. The system can also be integrated into existing arm prostheses to swing the arm through flexion/extension of a prosthetic elbow or shoulder joint.

Thus, unlike traditional systems, the proposed system can apply to individuals other than those with Parkinson's disease, specifically amputation as described. The proposed system also can also function with just one wearable device, rather than two that need to be worn on both arms. Additionally, the proposed software is simpler than existing techniques for detecting and classifying activities into walking vs. non-walking. The proposed software relies only on scalar signals (magnitude, energy, and power) to determine its control signal rather than vector quantities, and does not depend on explicitly sensing the gravity vector. Also, the proposed system is not only a device to provide a stimulus to the wearer to remind them to swing their arm, but can also be integrated into a motorized prosthetic elbow or shoulder to swing that elbow or shoulder in the absence of a physiological elbow or shoulder joint.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A limb activation system comprising:

at least one sensor configured to be coupled to a prosthetic arm of a user and configured to monitor movement of the user;

at least one motor configured to be coupled to the prosthetic arm, the at least one motor configured to cause the prosthetic arm to move in a cyclical motion;

a clutch configured to disengage the at least one motor; and a computing device operatively coupled to the at least one sensor, the at least one motor, and the clutch, the computing device comprising a memory and at least one processor, wherein the memory is configured to store computer-readable instructions and predetermined arm movement data patterns, wherein the predetermined arm movement data patterns include a kinematic relationship between walking speeds and elbow joint range-of-motion, wherein upon execution of the computer-readable instructions, the at least one processor is configured to:

cause a motion classifier to determine, based on data from one or more sensors of the at least one sensor, whether the user is engaged in walking, whether the user is engage in running, and whether the user is engaged in neither walking nor running, wherein the motion classifier is configured to generate an on signal when the motion classifier determines the user is engaged in walking or running, and wherein the motion classifier is configured to generate an off signal when the motion classifier determines the user is engaged in neither walking nor running;

cause a cadence detector to determine, based on data from one or more sensors of the at least one sensor, a step cadence of the user;

cause a trajectory generator to determine, based on the step cadence of the user and the predetermined arm movement data patterns, a cyclical trajectory of the prosthetic arm worn by the user when the motion classifier generates the on signal;

not cause the trajectory generator to determine the cyclical trajectory when the motion classifier generates the off signal, cause the motor to move the prosthetic arm of the user in the cyclical motion based on the cyclical trajectory, determine a difference between a desired prosthetic position based on the cyclical trajectory and an actual prosthetic position based on data from one or more sensors of the at least one sensor, cause the motor to move the prosthetic arm of the user in the cyclical motion based on the determined difference between the desired prosthetic position and the actual prosthetic position, and cause the clutch to disengage the motor when the motion classifier generates the off signal.

2. The system of claim 1, further comprising a sensory stimulator configured to be mounted to the user, wherein the on signal triggers the sensory stimulator to alert the user to perform movement during the walking or running.

3. The system of claim 2, wherein the sensory stimulator comprises a vibration stimulator, a pressure stimulator, a skin stretching stimulator, or an auditory stimulator.

4. The system of claim 1, wherein the computing device determines the step cadence of the walking or running based on the determined movement of the user, and wherein the on signal is generated based at least in part on the cadence of the walking or running.

5. The system of claim 4, wherein the at least one sensor generates a plurality of instantaneous acceleration signals, and wherein the computing device is configured to identify repetitive features in the instantaneous acceleration signals and a timing in between the repetitive features to determine the cadence.

6. The system of claim 1, wherein the at least one sensor comprises at least one of an accelerometer or a gyroscope.

7. The system of claim 1, wherein the at least one sensor is configured to provide frequency data, and wherein the determination that the user is engaged in walking or running is based on the frequency data.

8. The system of claim 1, wherein the computing device determines a window signal power based on the monitored movement, and wherein the determination that the user is engaged in walking or running is based on the window signal power.

9. The system of claim 1, wherein the at least one sensor comprises an accelerometer that generates an acceleration signal, and wherein the computing device is configured to process the acceleration signal to determine a single-sided frequency spectrum, wherein the computing device is configured to process the acceleration signal using a fast Fourier transform (FFT) or a machine learning algorithm.

10. The system of claim 9, wherein the computing device determines a proportion of the single-sided frequency spectrum that occurs in a time window by generating a first sum of magnitudes of frequency components in the time window and dividing the first sum by a second sum of magnitudes of frequency components across all frequencies.

11. A limb activation system comprising:

at least one sensor configured to be coupled to a prosthetic arm of a user and configured to monitor movement of the user wearing the prosthetic arm; and a computing device operatively coupled to the at least one sensor, the computing device comprising a memory and at least one processor, wherein the memory is configured to store computer-readable instructions and predetermined arm movement data patterns, wherein the predetermined arm movement data patterns includes a kinematic relationship between walking speeds and elbow joint range-of-motion, wherein upon execution of the computer-readable instructions, the at least one processor is configured to:

cause a motion classifier to determine, based on data from one or more sensors of the at least one sensor, whether the user is engaged in walking, whether the user is engaged in running, and whether the user is engaged in neither walking nor running, wherein the motion classifier is configured to generate an on signal when the motion classifier determines the user is engaged in walking or running, and wherein the motion classifier is configured to generate an off signal when the motion classifier determines the user is engaged in neither walking nor running;

cause a cadence detector to determine, based on data from one or more sensors of the at least one sensor, a step cadence of the user;

cause a trajectory generator to determine, based on the step cadence of the user and the predetermined arm movement data patterns, a cyclical trajectory of the prosthetic worn by the user when the motion classifier generates the on signal;

not cause the trajectory generator to determine the cyclical trajectory when the motion classifier generates the off signal, and cause movement of the prosthetic of the user in the cyclical motion based on the cyclical trajectory, determine a difference between a desired prosthetic position based on the cyclical trajectory and an actual prosthetic position based on data from one or more sensors of the at least one sensor, and cause the prosthetic arm of the user to move in the cyclical motion based on the difference.

12. The system of claim 11, further comprising a sensory stimulator configured to be mounted to the user, wherein the on signal triggers the sensory stimulator to alert the user to perform movement during the walking or running.

13. The system of claim 11, wherein the computing device determines the step cadence of the walking or running based on the determined movement of the user, and wherein the on signal is generated based at least in part on the cadence of the walking or running.

14. The system of claim 13, wherein the sensor generates a plurality of instantaneous acceleration signals, and wherein the computing device is configured to identify repetitive features in the instantaneous acceleration signals and a timing in between the repetitive features to determine the cadence.

15. The system of claim 11, wherein the sensor comprises at least one of an accelerometer or a gyroscope.

16. The system of claim 11, wherein the at least one sensor provides frequency data, and wherein the determination that the user is engaged in walking or running is based on the frequency data.

17. The system of claim 11, wherein the computing device determines a window signal power based on the monitored movement, and wherein the determination that the user is engaged in walking or running is based on the window signal power.

18. The system of claim 11, wherein the at least one sensor comprises an accelerometer that generates an acceleration signal, and wherein the computing device is configured to process the acceleration signal to determine a single-sided frequency spectrum, wherein the computing device is configured to process the acceleration signal using a fast Fourier transform (FFT) or a machine learning algorithm.

19. The system of claim 18, wherein the computing device determines a proportion of the single-sided frequency spectrum that occurs in a time window by generating a first sum of magnitudes of frequency components in the time window and dividing the first sum by a second sum of magnitudes of frequency components across all frequencies.

* * * * *